United States Patent [19]

Maignan et al.

[11] Patent Number: 4,851,541

[45] Date of Patent: Jul. 25, 1989

[54] PROCESS FOR THE PREPARATION OF A 4,5-TRI OR TETRAMETHYLENE-4-ISOTHIAZOLINE-3-ONE

[75] Inventors: Jean Maignan, Tremblay les Gonesse; Serge Restle, Aulnay Sous Bois; Michel Colin, Livry Gargan, all of France

[73] Assignee: Centre International de Recherches Dermatologiques (C.I.R.D.), Valbonne, France

[21] Appl. No.: 870,903

[22] Filed: Jun. 5, 1986

[30] Foreign Application Priority Data

Jun. 5, 1985 [FR] France .................................. 85 08469

[51] Int. Cl.$^4$ .................................................. C07D 275/04
[52] U.S. Cl. ...................................... 548/209; 564/189; 564/191
[58] Field of Search ................. 564/189, 191; 548/208, 548/209

[56] References Cited

U.S. PATENT DOCUMENTS

| | | | |
|---|---|---|---|
| 2,767,172 | 10/1956 | Katz et al. | 548/209 X |
| 3,012,039 | 12/1961 | Morley | 548/209 |
| 3,227,715 | 1/1966 | Bub | 548/209 X |
| 3,300,378 | 1/1967 | Fischer | 548/209 X |
| 3,362,992 | 1/1968 | Schwartz | 564/189 X |
| 3,661,974 | 5/1972 | Grivas | 548/209 X |
| 4,708,959 | 11/1987 | Shroot et al. | 548/209 X |

FOREIGN PATENT DOCUMENTS

| | | | |
|---|---|---|---|
| 234383 | 9/1959 | Australia | 548/209 |
| 58-177982 | 10/1983 | Japan | 548/209 |

OTHER PUBLICATIONS

Uchida et al, JCS Chem Comm., vol. of 1981, No. 10, pp. 510 and 511.
Baeckvall et al, Chemical Abstract, vol. 99, #176022s (1983).
Beak et al, J. Amer. Chem. Soc., vol. 107, pp. 4745 to 4756 (1985).
Huisgen et al, Chemical Abstracts, vol. 64, #9711–9712 (1966).

*Primary Examiner*—Floyd D. Higel
*Attorney, Agent, or Firm*—Cushman, Darby & Cushman

[57] ABSTRACT

A process for preparing a 4,5-tri or tetramethylene-4-isothiazoline-3-one comprises cyclizing a 2-alkyl or aralkyl thio-1-cycloalkene-1-carboxamide in the form of its sulfoxide in an organic solvent in the presence of a acid chloride and adding to the resulting 4,5-tri or tetramethylene-4-isothiazoline-3-one hydrochloride a mineral or organic base or water so as to free the 4,5-tri or tetramethylene-4-isothiazoline-3-one in the form of a free base.

3 Claims, No Drawings

PROCESS FOR THE PREPARATION OF A 4,5-TRI OR TETRAMETHYLENE-4-ISOTHIAZOLINE-3-ONE

The present invention relates to new compounds belonging to the class of 2-alkyl- or aralkyl-thio-1-cycloalkene-1-carboxamides, and ther sulfoxides; to processes for their preparation; and to their use as intermediates in the synthesis of 4,5-tri- and tetra-methylene-4-isothiazoline-3-ones.

4,5-tri- and tetramethylene-4-isothiazoline-3-ones, which are described in French Pat. No. 80.22278, are compounds which exhibit excellent antibacterial and antifungal activity. These compounds act not oonly on Gram positive bacteria and Gram negative bacteria, but also on yeasts and molds.

These compounds have, essentially, the following formula:

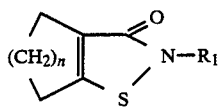

wherein
n is 1 or 2, and
$R_1$ represents (i) hydrogen, (ii) linear or branched alkyl having 1-12 carbon atoms, (iii) alkenyl having 3-6 carbon atoms, (iv) cycloalkyl having 3-6 carbon atoms, or (v) a radical of the formula

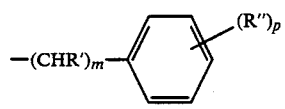

wherein m is 0 or 1, p is 1 or 2, R' represents hydrogen or lower alkyl and R" represents hydrogen, lower alkyl, $NO_2$, $-CF_3$ or halogen,
and the mineral or organic acid salts thereof.

In accordance with French Pat. No. 80.22278, the 4,5-tri-and tetra-methylene-4-isothiazoline-3-ones of Formula (I) are obtained according to the following reaction scheme:

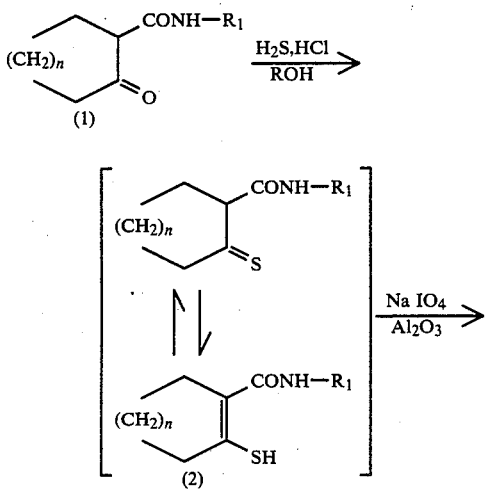

-continued

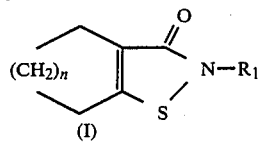

While this process gives good results with regard to ultimate yields, nonetheless it exhibits the disadvantage of being difficult to convert to an industrial scale.

The first step of this process, i.e. the production of 2-carbamoyl thiocyclanones (2) starting with 2-carbamoyl cyclanones (1) requires in effect the use of gaseous hydrogen sulfide and hydrochloric acid which, independent of the dangers associated with the use of these materials, causes under certain conditions, the precipitation of amides in the form of hydrochlorides so that the reaction can be incomplete.

Moreover, the second step, which consists in a cyclization reaction of 2-carbamoyl thiocyclanone (2) intermediates, is carried out in the presence of sodium metaperiodate fixed on acid alumina, which can make this reaction particularly dangerous when it is carried out in large amounts.

After various studies, it has been noted that the 2-alkyl- or aralkyl-thio-1-cycloalkene-1-carboxamides constitute easily accessible and particularly appropriate intermediates for the preparation, on a large scale, of 4,5-tri and tetramethylene-4-isothiazoline-3-ones.

The present invention thus relates to 2-alkyl or aralkyl-1-cycloalkene-1-carboxamides having the formula

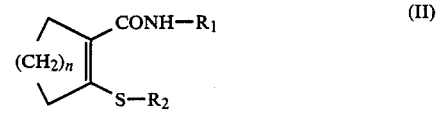

wherein
n is 1 or 2,
$R_2$ represents alkyl having 1-12 carbon atoms or aralkyl, and
$R_1$ represents (i) hydrogen, (ii) linear or branched alkyl having 1-12 carbon atoms, (iii) alkenyl having 3-6 carbon atoms, (iv) cycloalkyl havng 3-6 carbon atoms, or (v) a radical of the formula

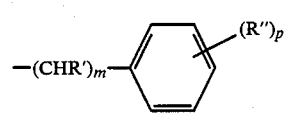

wherein m is 0 or 1, p is 1 or 2, R' represents hydrogen or lower alkyl and R" represents hydrogen, lower alkyl, $NO_2$, $-CF_3$ or halogen, and the sulfoxides of the compounds of Formula II.

By linear or branched alkyl having 1-12 carbon atoms is meant, particularly, methyl, ethyl, propyl, isopropyl, butyl, isobutyl, tert.butyl, hexyl, octyl, decyl or dodecyl radicals.

Representative alkenyl radicals having 3-6 carbon atoms include, particularly, allyl and 2-butenyl radicals.

By cycloalkyl is meant cyclopropyl, cyclobutyl, cyclopentyl or cyclohexyl.

When $R_1$ represents a radical of the formula

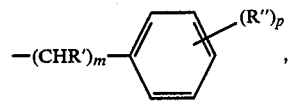

it can be phenyl, p-chlorophenyl, 2,4-dichlorophenyl, benzyl, p-chlorobenzyl or 2,4-dichlorobenzyl.

A preferred aralkyl radical is benzyl.

Representative compounds of Formula (II), in accordance with the present invention, which are capable of acting as starting products or intermediates in the synthesis of 4,5-tri- and tetramethylene-4-isothiazoline-3-ones include, particularly, the following:

| Compound No. | | n | $R_1$ | $R_2$ |
|---|---|---|---|---|
| (1) | 2-benzylthio-1-cyclopentene-1-carboxamide | 1 | H | $-CH_2C_6H_5$ |
| (2) | 2-N—methyl benzylthio-1-cyclopentene-1-carboxamide | 1 | $-CH_3$ | $-CH_2C_6H_5$ |
| (3) | 2-N—ethyl benzylthio-1-cyclopentene-1-carboxamide | 1 | $-C_2H_5$ | $-CH_2C_6H_3$ |
| (4) | 2-N—butyl benzylthio-1-cyclopentene-1-carboxamide | 1 | $-nC_4H_9$ | $-CH_2C_6H_5$ |
| (5) | 2-N—tert.butyl benzylthio-1-cyclopentene-1-carboxamide | 1 | tert-$C_4H_9$ | $-CH_2C_6H_5$ |
| (6) | 2-N—isopropyl benzylthio-1-cyclopentene-1-carboxamide | 1 | $-isoC_3H_7$ | $-CH_2C_6H_5$ |
| (7) | 2-N—hexyl benzylthio-1-cyclopentene-1-carboxamide | 1 | $-C_6H_{13}$ | $-CH_2C_6H_5$ |
| (8) | 2-N—octyl benzylthio-1-cyclopentene-1-carboxamide | 1 | $-nC_8H_{17}$ | $-CH_2C_6H_5$ |
| (9) | 2-N—decyl benzylthio-1-cyclopentene-1-carboxamide | 1 | $-C_{10}H_{21}$ | $-CH_2C_6H_5$ |
| (10) | 2-N—dodecyl benzylthio-1-cyclopentene-1-carboxamide | 1 | $-C_{12}H_{25}$ | $-CH_2C_6H_5$ |
| (11) | 2-N—alkyl benzylthio-1-cyclopentene-1-carboxamide | 1 | $-CH_2-CH=CH_2$ | $-CH_2C_6H_5$ |
| (12) | 2-N—cyclohexyl benzylthio-1-cyclopentene-1-carboxamide | 1 | $-C_6H_{11}$ | $-CH_2C_6H_5$ |
| (13) | 2-N—p-chlorophenyl benzylthio-cyclopentene-1-carboxamide | 1 | $-C_6H_4p$-Cl | $-CH_2C_6H_5$ |
| (14) | 2-N—p-chlorobenzyl benzylthio-1-cyclopentene-1-carboxamide | 1 | $-CH_2C_6H_4p$-Cl | $-CH_2C_6H_5$ |
| (15) | 2',4'-N—dichloro-2-benzyl benzylthio-1-cyclopentene-1-carboxamide | 1 | $-CH_2C_6H_3Cl_2$ | $-CH_2C_6H_5$ | and the sulfoxides of these compounds.

The present invention also relates to the processes for the preparation of the compounds of Formula II such as defined above.

These compounds can be obtained by one or the other of two synthesis methods represented by the following reaction scheme:

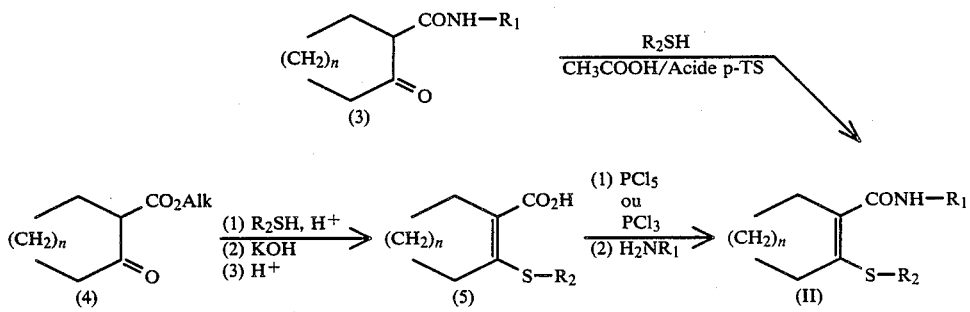

The first synthesis method comprises treating, at ambient temperature and with stirring, a 2-carbamoyl cyclanone (3) with an alkyl or aralkyl mercaptan having a free proton which is α to the thiol function, in an acid medium, preferably in an acetic acid/p-toluene sulfonic acid medium.

The 2-carbamoyl cyclanones (3), as initial reactants, are obtained either by the method described by Ch. Bischoff and H. Herma, J. F. Prakt. Chemie, 318, 773-778 (1976) when $R_1$=H, or by the method described by S. Hunig et al., Chem. Ber. 95, 926-936 (1962) when $R_1 \neq H$.

The second synthesis method comprises treating an alkyl cyclanone carboxylate (4) in an acid medium with an alkyl or aralkyl mercaptan, such as defined above, and saponifying in-situ the ester function so as to obtain the 2-alkyl or aralkyl thio-1-cycloalkene-1-carboxylic acid of formula (5) with a yield greater than 80%.

The latter compound is transformed into the corresponding acid chloride which is then amidified in-situ by reacting it, optionally in the presence of triethylamine, with a primary amine of the formula, $R_1NH_2$. When the reaction is carried out in the absence of triethylamine, an excess of the primary amine is employed.

This second synthesis method is particularly preferred for it is carried out starting with easily available products such as alkyl cyclopentanone or cyclohexanone carboxylates. Moreover, the intermediate compound of formula (5) rapidly and with good yields leads to compounds of formula (II) having the various meanings of the $R_1$ radical.

The sulfoxides of the compounds of formula (II) are obtained by the action of m-chloroperbenzoic acid or by the action of $H_2O_2$ in acid medium, the reaction then being either conducted in formic acid for the most polar amides, or in a mixture of methylene chloride containing about 20% by volume of formic acid for the less polar amides.

The present invention also relates to a process for the preparation of 4,5-tri- and tetra-methylene-4-isothiazoline-3-ones of Formula (I), such as defined above, starting with the 2-alkyl or aralkyl thio-1-cycloalkene-1-carboxamides of Formula (II).

This process can be represented by the following reaction scheme:

$$(CH_2)_n \begin{array}{c} CONH-R_1 \\ \diagdown \\ S-R_2 \\ \downarrow \\ O \end{array} \xrightarrow{SOCl_2}$$

(II')

$$(CH_2)_n \begin{array}{c} OH \\ \diagdown \\ \oplus N-R_1 \\ / \\ S \end{array} Cl^\ominus \longrightarrow$$

(6)

$$(CH_2)_n \begin{array}{c} O \\ \parallel \\ \diagdown \\ / N-R_1 \\ S \end{array}$$

(I)

The cyclization reaction of the sulfoxides of Formula (II'), to obtain the hydrochlorides of the 4,5-tri or tetramethylene-4-isothiazoline-3-ones of formula (6), is preferably carried out in an organic solvent such as, for example, methylene chloride, in the presence of an acid chloride such as thionyl chloride.

The hydrochlorides are particularly stable and can be stored for long periods of time without requiring any particular storage conditions.

On treating the hydrochlorides with a mineral or organic base, the 4,5-tri or tetramethylene-4-isothiazoline-3-ones are liberated in the form of bases. For the very lipophilic hydrochlorides, several water washings with a solution of the hydrochloride in methylene chloride suffice to displace the hydrochloric acid.

The process as described above provides the following 4,5-tri- and tetra-methylene-4-isothiazoline-3-ones:
4,5-trimethylene-4-isothiazoline-3-one,
2-methyl-4,5-trimethylene-4-isothiazoline-3-one,
2-ethyl-4,5-trimethylene-4-isothiazoline-3-one,
2-n-butyl-4,5-trimethylene-4-isothiazoline-3-one,
2-tert.butyl-4,5-trimethylene-4-isothiazoline-3-one,
2-isopropyl-4,5-trimethylene-4-isothiazoline-3-one,
2-n-hexyl-4,5-trimethylene-4-isothiazoline-3-one,
2-octyl-4,5-trimethylene-4-isothiazoline-3-one,
2-decyl-4,5-trimethylene-4-isothiazoline-3-one,
2-dodecyl-4,5-trimethylene-4-isothiazoline-3-one,
2-allyl-4,5-trimethylene-4-isothiazoline-3-one,
2-cyclohexyl-4,5-trimethylene-4-isothiazoline-3-one,
2-p-chlorophenyl-4,5-trimethylene-4-isothiazoline-3-one,
2-p-chlorobenzyl-4,5-trimethylene-4-isothiazoline-3-one and
2',4'-dichloro-2-benzyl-4,5-trimethylene-4-isothiazoline-3-one.

As described in French Pat. No. 80.22278, the 4,5-tri and tetramethylene-4-isothiazoline-3-ones of Formula (I) in which the $R_1$ radical represents either a mono- or dihydroxy alkyl radical, or a N-substituted carbamoyl radical, are prepared preferably by reacting respectively, in a basic catalyst, an oxirane (substituted or not) or an N-substituted isocyanate with the 4,5-tri or tetramethylene-4-isothiazoline-3-one.

The following non-limiting examples are given to illustrate the preparation of 2-alkyl and aralkyl thio-1-cycloalkylene-1-carboxamides of Formula (II), as well as the preparation of several 4,5-tri and tetramethylene-4-isothiazoline-3-ones.

I—Preparation of 2-alkyl and aralkyl thio-1-cycloalkene-1-carboxamides of Formula (II).

EXAMPLE 1

Preparation of 2-benzylthio-1-cyclopentene-1-carboxamide and its sulfoxide-(Formula II with $R_1$=H and $R_2$=—$CH_2C_6H_5$)

(a) 2-benzylthio-1-cyclopentene-1-carboxamide

To a solution, stirred at ambient temperature and under an inert atmosphere, of 381 g of 2-carboxamide cyclopentanone and 570 g of p-toluenesulfonic acid (monohydrate) in 2,500 cm$^3$ of acetic acid, there are slowly added 360 cm$^3$ of benzylmercaptan.

The reaction mixture is then left overnight at ambient temperature. The solution is then concentrated under reduced pressure, and poured into water. The pH of the resulting suspension is adjusted to about 5 by the addition of sodium bicarbonate. The resulting product is filtered, washed twice with water and then dried, yielding 55 g of 2-benzylthio-1-cyclopentene-1-carboxamide in the form of white crystals.

The NMR $^1$H spectrum corresponds to the expected structure.

(b) 2-benzylsulfinyl-1-cyclopentene-1-carboxamide

To a solution, stirred at 0° C., of 480 g of 2-benzylthio-1-cyclopentene-1-carboxamide, obtained above, in 2,000 cm$^3$ of formic acid, there are slowly added 216 cm$^3$ of 30% $H_2O_2$. At the end of the reaction, the reaction mixture is stirred at a temperature between 20° and 30°. This oxidation reaction is monitored by thin layer chromatography (TLC). When all of the thioether has been transformed into the corresponding sulfoxide, the solution is concentrated and then poured into water. The product precipitates and the resulting suspension is neutralized by the addition of 5N soda. The resulting solid is filtered, washed several times with water, then dried and finely divided by stirring in a mixture of one liter of ether and 300 cm$^3$ of acetonitrile.

The white cyrstals are filtered and dried yielding 450 g of 2-benzylsulfinyl-1-cyclopentene-1-carboxamide in the form of a white solid having a melting point of 174° C.

The NMR $^1$H and infrared spectra correspond to the expected structure.

Elemental analysis: $C_{13}H_{15}NO_2S$;
Calculated: C 62.62; H 6.06; N 5.62; S 12.86;
Found: C 62.15; H 6.08; N 5.55; S 12.74.

EXAMPLE 2

Preparation of
2-N-methyl-benzylthio-1-cyclopentene-1-carboxamide
and its sulfoxide (Formula II with $R_1=CH_3$ and
$R_2=-CH_2C_6H_5$)

(a) 2-benzylthio-1-cyclopentene-1-carboxylic acid

Into a stirred solution of 1 liter of benzylmercaptan and 1,250 kg of ethyl cyclopentanone carboxylate in 2 liters of absolute alcohol, there is passed a current of HCl gas. The reaction is exothermic and the temperature is controlled so as to maintain it lower than 40° C. by regulating the delivery of the HCl gas. One half hour later, about 300 g HCl have been absorbed.

Stirring is maintained for about one hour and it is verified, by thin layer chromatography (TLC), that the ethyl cyclopentanone carboxylate has been completely transformed into the corresponding thioether. The formation of two phases is noted, the lower phase corresponding to the condensation product.

There is then introduced, at ambient temperature, 1 kg of potash dissolved in 1.5 liters of water. The mixture is adjusted to a temperature between 70° and 75° C. until the reaction mixture becomes homogeneous and until there is a complete disappearance (monitored by TLC) of the condensation product, which takes about 2 hours.

To this mixture, cooled to about 0° C., there are then added initially 2 liters of 5N HCl and then 2 liters of water. The precipitate which forms is filtered, washed first with water, then with 1 liter of cold alcohol and finally dried under reduced pressure, yielding 1.6 kg of 2-benzylthio-1-cyclopentene-1-carboxylic acid in the form of white crystals having a melting point of 233° C.

Elemental analysis: $C_{13}H_{14}O_2S$;
Calculated: C 66.63; H 6.02; O 13.66; S 13.68;
Found: C 66.88; H 5.97; O 13.90; S 13.59.

(b) 2-N-methyl benzylthio-1-cyclopentene-1-carboxamide

To a stirred suspension, at ambient temperature and under an inert atmosphere, of 234.32 g of the 2-benzylthio-1-cyclopentene-1-carboxylic acid, obtained above, in 1.5 liters of anhydrous methylene chloride, there are rapidly added 87 cm³ of phosphorus trichloride. At the end of the addition, the mixture is held under reflux for 3½ hours. After cooling the mixture to 0° C., the acid chloride crystallizes and to the resulting suspension there is added an excess of methylamine in aqueous solution (375 cm³ of a 40% solution).

The reaction is very exothermic. One hour after having completed the introduction of the methylamine, the termination of the reaction is verified by TLC.

The methylene chloride phase is decanted, washed with water, dried over magnesium sulfate and the solvent is removed under reduced pressure. On cooling, the product crystallizes and is dispersed, with stirring, in 400 cm³ of ether. The 2-N-methyl benzylthio-1-cyclopentene-1-carboxamide is filtered and then dried, yielding 177 g of crude amide whose NMR ¹H spectrum corresponds to the expected structure.

(c) 2-N-methyl benzylsulfinyl-1-cyclopentene-1-carboxamide

To a solution of 166.3 g of 2-N-methyl benzylthio-1-cyclopentene-1-carboxamide, obtained above, in 1.5 liters of methylene chloride stirred at 0° C. under an inert atmosphere, there are added, by portions, 132 g of m-chloroperbenzoic acid.

When all of the starting thioether is transformed into the corresponding sulfoxide, the solution is washed twice with an aqueous solution of sodium bisulfite, once with sodium bicarbonate and then with water. The organic phase is dried over sodium sulfate and concentrated. On recrystallization of the resulting product in 300 cm³ of toluene, 81 g of the expected sulfoxide are isolated.

To the stirred filtrate 700 cm³ of isopropyl ether are added and 70 g of sulfoxide are again recovered.

The 2-N-methyl benzylsulfinyl-1-cyclopentene-1-carboxamide is a white product having a melting point of 128° C. The NMR ¹H spectrum corresponds to the expected structure.

Elemental analysis: $C_{14}H_{17}NO_2S$;
Calculated: C 63.85; H 6.51; N 5.32; O 12.15; S 12.17;
Found: C 63.78; H 6.46; N 5.29; O 12.40; S 12.01.

EXAMPLE 3

Preparation of 2-N-ethyl
benzylthio-1-cyclopentene-1-carboxamide and its
sulfoxide (Formula II with $R_1=-C_2H_5$ and
$R_2=-CH_2C_6H_5$)

(a) 2-N-ethyl benzylthio-1-cyclopentene-1-carboxamide

In accordance with the same procedures described in Example 2(b), 234 g of 2-benzylthio-1-cyclopentene-1-carboxylic acid, obtained in Example 2(a), are treated with 87 cm³ of phosphorus trichloride. To the resulting acid chloride there are then added 600 cm³ of a 33% aqueous solution of ethylamine.

The organic phase is then treated as in Example 2(b), yielding 189 g of crude 2-N-ethyl benzylthio cyclopentene carboxamide which is then recrystallized in toluene, yielding 152 g of white crystals whose NMR ¹H spectrum corresponds to the expected structure.

(b) 2-N-ethyl benzylsulfinyl-1-cyclopentene-1-carboxamide 95 g of 2-N-ethylbenzylthio-1-cyclopentene-1-carboxamide, obtained above, are treated in 550 cm³ of formic acid with 37 cm³ of $H_2O_2$ (110 vol) at a temperature of about 10° C. At the end of the reaction, the reaction medium is treated as in Example 2(c). The crude sulfoxide is stirred in 150 cm³ of isopropyl ether, then filtered and dried, yielding 75 g of 2-N-ethyl benzylsulfinyl-1-cyclopentene-1-carboxamide in the form of white crystals having a melting point of 115° C.

The NMR ¹H and IR spectra correspond to the expected structure.

Elemental analysis: $C_{15}H_{19}NO_2S$;
Calculated: C 64.95; H 6.90; N 5.05; O 11.54;
Found: C 64.95; H 7.04; N 5.17; O 11.24.

EXAMPLE 4

Preparation of 2-N-butyl
benzylthio-1-cyclopentene-1-carboxamide and its
sulfoxide (Formula II with $R_1=n-C_4H_9$ and
$R_2=-CH_2C_6H_5$)

(a) 2-N-butyl benzylthio-1-cyclopentene-1-carboxamide

In accordance with the same procedures described in Example 2(b), 200 g of 2-benzyl thiocyclopentene carboxylic acid, obtained in Example 2(a), in 1.2 liters of methylene chloride are treated with 55 cm³ of phosphorus trichloride. To the acid chloride formed there is then added, over a one-half hour period, a mixture of 125 cm³ of n-butylamine and 300 cm³ of triethylamine.

The reaction mixture is then cooled to 0° C. and 400 cm³ of 2N HCl are added with vigorous stirring. The organic phase is decanted, washed with water and then dried over magnesium sulfate.

After evaporation of the solvent under a vacuum, 240 g of crude amide are obtained in the form of a beige colored pasty solid that is directly used in the following step after having verified that its NMR $^1$H spectrum corresponds indeed to the expected structure.

(b) 2-N-butyl benzylsulfinyl-1-cyclopentene-1-carboxamide.

In accordance with the same procedures described in Example 3(b), 289 g of the thioether, obtained above, in 1,500 cm$^3$ of formic acid are treated with 102 cm$^3$ of H$_2$O$_2$ (110 vol), in a manner so that the temperature remains lower than 20° C.

After treatment under these conditions, 210 g of 2-N-butyl benzylsulfinyl-1-cyclopentene-1-carboxamide in the form of white crystals having a melting point of 125° C. are obtained.

The IR and NMR $^1$H spectra correspond to the expected structure.

Elemental Analysis: C$_{17}$H$_{23}$NO$_2$S;
Calculated: C 66.85; H 7.59; N 4.58; O 10.47; S 10.49;
Found: C 66.92; H 7.63; N 4.62; O 10.59; S 10.40.

EXAMPLE 5

Preparation of 2-tert.butyl benzylthio-1-cyclopentene-1-carboxamide and its sulfoxide (Formula II with R$_1$=tert.C$_4$H$_9$ and R$_2$=—CH$_2$C$_6$H$_5$)

(a) 2-N-tert.butyl benzylthio-1-cyclopentene-1-carboxamide

To a suspension of 75 g of 2-benzylthio cyclopentene carboxylic acid obtained in Example 2(a) in 600 cm$^3$ of anhydrous methylene chloride, there are slowly added, at 0° C. and under an inert atmosphere, 20 cm$^3$ of phosphorus trichloride. The mixture is then held at reflux for three hours, after which it is left overnight at ambient temperature. There is then added, at 0° C. with stirring, a mixture of 115 cm$^3$ of triethylamine and 40.5 cm$^3$ of tert. butylamine. The reaction mixture is stirred for one hour at ambient temperature and then poured into 1.5 liters of water. The organic phase is decanted, washed twice with water, dried over magnesium sulfate and concentrated under reduced pressure, yielding a crude solid whose NMR (CDCl$_3$) spectrum corresponds to the expected structure. This amide is used as such for the following procedure.

(b) 2-N-tert.butyl benzylsufinyl-1-cyclopentene-1-carboxamide

To a solution of all of the preceding product in a mixture of 500 cm$^3$ of methylene chloride and 100 cm$^3$ of formic acid there are slowly added, with stirring and at a temperature of 0° C., 31 cm$^3$ of H$_2$O$_2$ (9.8N). Stirring is continued for three hours at 0° C. and the reaction mixture is then left overnight at ambient temperature.

It is then verified, at this stage by TLC, that all of the thioether has been transformed into the corresponding sulfoxide.

The reaction mixture is then poured into one liter of water and the methylene chloride phase is decanted, washed with water, dried over magnesium sulfate and then concentrated to dryness.

The resulting crude solid is then recrystallized in 300 cm$^3$ of toluene, yielding 64.5 g of white crystals having a melting point of 154° C.

Elemental analysis: C$_{17}$H$_{23}$NO$_2$S;
Calculated: C 66.85; H 7.59; N 4.59; S 10.50;
Found: C 66.79; H 7.59; N 4.63; S 10.66.

EXAMPLE 6

Preparation of 2-N-isopropyl benzylthio-1-cyclopentene-1-carboxamide and its sulfoxide (Formula II with R$_1$=isoC$_3$H$_7$ and R$_2$=—CH$_2$C$_6$H$_5$)

(a) 2-N-isopropyl benzylthio-1-cyclopentene-1-carboxamide.

In accordance with the same procedures described in Example 2(b), 234.3 g of 2-benzylthio-1-cyclopentene-1-carboxylic acid, obtained in Example 2(a), are treated with 87 cm$^3$ of phosphorus trichloride.

To this resulting acid chloride, there is then added at 0° C. a mixture of 128 cm$^3$ of isopropylamine and 351 cm$^3$ of triethylamine.

Stirring is continued after the end of the addition of 1 hour and there are then added 200 cm$^3$ of 2N HCl. The methylene chloride phase is decanted, washed again with 200 cm$^3$ of 2N HCl, then twice with water. After drying over magnesium sulfate, the solvent is evaporated under reduced pressure, yielding the crude amide which is directly oxidized to its corresponding sulfoxide after having verified that its NMR $^1$H spectrum corresponds to the expected structure.

(b) 2-N-isopropyl benzylsulfinyl-1-cyclopentene-1-carboxamide.

In accordance with the same procedures described in Example 3(b), the thioether obtained above, dissolved in 1.5 liters of formic acid, is treated with 97 cm$^3$ of H$_2$O$_2$ (110 vol) at a temperature near 10° C.

At the end of the reaction, thiosulfate is added to destroy the excess H$_2$O$_2$. The formic acid is evaporated and the reaction mixture is then treated in accordance with the same operation described in Example 3(b).

The resulting solid is recrystallized in isopropyl ether, then washed with acetonitrile, yielding 162 g of 2-N-isopropyl benzylsulfinyl-1-cyclopentene-1-carboxamide in the form of white crystals having a melting point of 158° C.

The IR and NMR spectra correspond to the expected structure.

Elemental analysis: C$_{16}$H$_{21}$NO$_2$S;
Calculated: C 65.94; H 7.26; N 4.81; O 10.98; S 11.90;
Found: C 65.36; H 7.29; N 4.74; O 11.40; S 10.82.

EXAMPLE 7

Preparation of 2-N-hexyl benzylthio-1-cyclopentene-1-carboxamide and its sulfoxide (Formula II with R$_1$=n—C$_6$H$_{13}$ and R$_2$=—CH$_2$C$_6$H$_5$)

(a) 2-N-hexyl benzylthio-1-cyclopentene-1-carboxamide

A suspension of 234.3 g of 2-benzylthio-1-cyclopentene carboxylic acid, obtained in Example 2(a) and stirred in 1.5 liters of methylene chloride, is treated with 75 cm$^3$ of phosphorus trichloride.

After 3 hours under reflux, the mixture is cooled to 0° C. There is then slowly added a mixture of 159 cm$^3$ of hexylamine and 351 cm of triethylamine. The mixture, after the end of the addition, is stirred for 3 hours at ambient temperature, then washed initially with 2N HCl and finally with water.

The organic phase is dried over magnesium sulfate, filtered and the filtrate concentrated under reduced pressure, yielding a viscous liquid whose NMR $^1$H spectrum corresponds to the expected structure.

(b) 2-N-hexyl benzylsulfinyl-1-cyclopentene-1-carboxamide

A solution of 254 g of the preceding product, stirred in 1 liter of formic acid, is cooled to 0° C. There are then slowly added 75 cm$^3$ of H$_2$O$_2$. After the end of the addition, the reaction mixture is again stirred for 2 hours, then left overnight at ambient temperature. The formic acid is removed by evaporation under a vacuum. The resulting liquid is dissolved in 1 liter of methylene chloride. This solution is washed with dilute soda, then with water and finally dried over magnesium sulfate. It is concentrated, then deposited on a silica gel column. The expected product is eluted with a methylene chloride, ethyl acetate and methanol mixture. After concentration of the elution phases, 210 g of the sulfoxide in the form of white crystals having a melting point of 70° C. are obtained.

Elemental analysis: $C_{19}H_{27}NO_2S$;
Calculated: C 68.43; H 8.16; N 4.20; S 9.61;
Found: C 68.51; H 8.22; N 4.15; S 9.53.

EXAMPLE 8

Preparation of 2-N-octyl benzylthio-1-cyclopentene-1-carboxamide and its sulfoxide (Formula II with $R_1=C_8H_{17}$ and $R_2=—CH_2C_6H_5$)

(a) 2-N-octyl benzylthio-1-cyclopentene-1-carboxamide

To a stirred suspension of 1 kg of 2-benzylthio-1-cyclopentene-1-carboxylic acid, obtained in Example 2(a), in 66 liters of methylene chloride, there are slowly added, under an inert atmosphere, 275 cm$^3$ of phosphorus trichloride.

The mixture is then held at the reflux of the dichloromethane for 3 hours at which point the mixture becomes homogeneous. At this state, it is verified by TLC that the transformation of the acid into the corresponding acid chloride is complete. (About 0.5 cm$^3$ of the reaction mixture is withdrawn and poured into 2 cm$^3$ of anhydrous methanol, the resulting methyl ester being then deposited on the plate).

The mixture is then cooled to 0° C. and the acid chloride crystallizes, under vigorous stirring. A mixture of 850 cm$^3$ of octylamine and 1.5 liters of triethylamine is added over about a one half hour period while maintaining the temperature lower than 20° C.

The reaction mixture becomes progressively homogeneous and is left at ambient temperature for about 1 hour after the end of the introduction.

By TLC it is verified that the reaction is terminated. To the mixture cooled to 0° C. there are then added 2 liters of 2N HCl.

The organic phase is decanted, washed three times with water, dried over magnesium sulfate and the solvent evaporated under reduced pressure.

The crude amide obtained in the form of a viscous liquid is poured, with stirring, into 10 liters of hexane. The resulting emulsion is cooled to 0° C. The product crystallizes in the form of a beige colored pasty solid. It is filtered and dried yielding 1.3 kg of 2-N-octyl benzylthio-1-cyclopentene-1-carboxamide that is used directly for the following step.

(b) 2-N-octyl benzylsulfinyl-1-cyclopentene-1-carboxamide.

2.8 kg of 2-N-octyl benzylthio-1-cyclopentene-1-carboxamide, in a mixture of 11 liters of methylene chloride and 2.5 liters of formic acid, are treated with 785 cm$^3$ of H$_2$O$_2$ (110 vol).

Stirring of the reaction mixture is continued for 2 hours at ambient temperature, at which point 10 liters of water are added with stirring. The organic phase is decanted, washed with sodium bicarbonate, then with water and dried over magnesium sulfate. After treatment of the crude sulfoxide, as in Exmaple 3(b), 1.6 kg of 2-N-octyl benzylsulfinyl-1-cyclopentene-1-carboxamide in the form of a white crystallized product having a melting point of 81° C. are obtained.

Elemental analysis: $C_{21}H_{31}NO_2S$;
Calculated: C 69.76; H 8.64; N 3.87; O 8.85; S 8.87;
Found: C 69.81; H 8.60; N 3.86; O 9.01; S 8.83.

EXAMPLE 9

Preparation of 2-N-decyl benzylthio-1-cyclopentene-1-carboxamide and its sulfoxide (Formula II with $R_1=C_{10}H_{21}$ (n) and $R_2=—CH_2—C_6H_5$)

(a) 2-N-decyl benzylthio-1-cyclopentene-1-carboxamide.

To a suspension of 77 g of 2-benzylthio cyclopentene carboxylic acid, obtained in Example 2(a), in 600 cm$^3$ of methylene chloride, stirred at 0° C., there are slowly added 20 cm$^3$ of phosphorus trichloride. At the end of the addition, the reaction mixture is held for 3 hours at reflux, then left overnight at ambient temperature. Finally, at a temperature of 0° C., there is slowly added to the reaction mixture, a mixture of 80 cm$^3$ of (n) decylamine and 110 cm$^3$ of triethylamine. The mixture is then stirred for three hours at ambient temperature and poured over 1 liter of iced water. The organic phase is decanted, washed twice with water and dried over sodium sulfate. The solvent is removed by evaporation under a vacuum, yielding 130 g of a viscous liquid at ambient temperature whose NMR $^1$H spectrum, 80 MHz, corresponds to the expected structure.

(b) 2-N-decyl benzylsulfinyl-1-cyclopentene-1-carboxamide.

A mixture of 120 g of the preceding amide in 350 cm$^3$ of methylene chloride and 90 cm$^3$ of formic acid is stirred at 0° C. There are then added 32.5 cm$^3$ of H$_2$O$_2$ (9.8 N). Stirring is continued for 1 hour at 0° C. and then for 3 hours at ambient temperature. The mixture is poured into 500 cm$^3$ of water. The organic phase is decanted, washed with a 10% aqueous solution of bicarbonate, then with water and dried over magnesium sulfate. The solvent is removed by evaporation under a vacuum. The resulting product is treated with animal charcoal in 200 cm$^3$ of isopropyl ether at the boil. To the filtered solution 250 cm$^3$ of hexane are added and the temperature of the resulting mixture is adjusted to $-20°$ C.

The crystallized product is filtered and dried, yielding 50 g of white crystals having a melting point of 65° C.

Elemental analysis: $C_{23}H_{35}NO_2S$;
Calculated: C 70.90; H 9.05; N 3.60; S 8.23;
Found: C 70.50; H 9.08; N 3.57; S 8.17.

EXAMPLE 10

Preparation of 2-N-dodecyl benzylthio-1-cyclopentene-1-carboxamide and its sulfoxide (Formula II with $R=C_{12}H_{25}$ and $R_2=-CH_2C_6H_5$)

(a) 2-N-dodecyl benzylthio-1-cyclopentene-1-carboxamide 100 g of 2-benzylthio-1-cyclopentene-1-carboxylic acid, obtained in Example 2(a), in 400 cm³ of methylene chloride, are treated with 27.45 cm³ of phosphorus trichloride. At the end of the addition, the reaction mixture is held under reflux for 3 hours 30 minutes. At this stage all of the acid is transformed and the mixture is homogeneous.

To the resulting acid chloride there is added, while maintaining the temperature lower than 0° C., a mixture of 95 g of (n) dodecylamine and 150 cm³ of triethylamine in 400 cm³ of anhydrous methylene chloride. At the end of the reaction 200 cm³ of 2N HCl are added.

After decanting and washing the organic phase with HCl and water, drying over magnesium sulfate and concentrating under a vacuum, 2-N-dodecyl benzylthio-1-cyclopentene-1-carboxamide is obtained in the form of a viscous liquid which is directly oxidized into the corresponding sulfoxide.

(b) 2-N-dodecyl benzylsulfinyl-1-cyclopentene-1-carboxamide

The thioether, obtained above, in a mixture of 800 cm³ of methylene chloride and 200 cm³ of formic acid, is treated at 0° C. with 38.5 cm³ of $H_2O_2$ (110 vol). At the end of the reaction the mixture is poured into 500 cm³ of water and the organic phase is decanted.

After treatment under the same conditions as in Example 6(b), a viscous liquid is isolated which is then crystallized in a mixture of 800 cm³ of hexane and 200 cm³ of isopropyl ether, yielding 102 g of 2-N-dodecyl benzylsulfinyl-1-cyclopentene-1-carboxamide in the form of white crystals having a melting point of 68° C.

The IR and NMR $^1H$ spectra correspond to the expected structure.

Elemental analysis: $C_{25}H_{39}NO_2S$;
Calculated: C 71.89; H 9.41; N 3.55; O 7.66; S 7.68;
Found: C 71.93; H 9.35; N 3.38; O 7.66; S 7.55.

EXAMPLE 11

Preparation of 2-N-allyl benzylthio-1-cyclopentene-1-carboxamide and its sulfoxide (Formula II with $R_1$=allyl and $R_2=-CH_2-C_6H_5$)

(a) 2-N-allyl benzylthio-1-cyclopentene-1-carboxamide.

A suspension of 55 g of 2-benzylthio cyclopentene carboxylic acid, obtained in Example 2(a), in 300 cm³ of methylene chloride is treated with 16 cm³ of phosphorus trichloride. At the end of the addition the mixture is held under reflux for three hours. Then, at a temperature of 0° C., there is added, with stirring, a mixture of 82 cm³ of triethylamine and 22.5 cm³ of allylamine. The mixture is then left overnight at ambient temperature. The mixture is then poured into a liter of ice water and the methylene chloride phase is decanted, washed twice with water, dried over sodium sulfate and then concentrated. The resulting product in the form of a viscous liquid is dissolved in 700 cm³ of ethyl ether and the resulting solution is treated with animal charcoal. The reaction mixture is then filtered on paper and the solvent evaporated. 2-N-allyl benzylthio-1-cyclopentene-1-carboxamide is thus obtained in the form of a yellow-brown liquid that is used directly for the synthesis of its sulfoxide.

(b) 2-N-allyl benzylsufinyl-1-cyclopentene-1-carboxamide 57 g of the preceding crude product are treated with stirring at 0° C. in a mixture of 270 cm³ of methylene chloride and 30 cm³ of formic acid with 19.5 cm³ of $H_2O_2$ (9.8 N). After 3 hours of stirring the reaction mixture is left overnight at ambient temperature. The next day, the mixture is poured into 700 cm³ of ice water and the methylene chloride phase is decanted, washed twice with bicarbonated water (10%), then with water. After drying over magnesium sulfate and concentration, 51 g of crude product are obtained. This crude product is recrystallized in 300 cm³ of isopropyl ether. The resulting crystals are filtered and dried, yielding 42.5 g of 2-N-allyl benzylsulfinyl-1-cyclopentene-1-carboxamide in the form of white crystals having a melting point of 112° C.

Elemental analysis: $C_{16}H_{19}NO_2S$;
Calculated: C 66.40; H 6.62; N 4.84; S 11.08;
Found: C 66.46; H 6.68; N 4.73; S 10.97.

EXAMPLE 12

Preparation of 2-N-cyclohexyl benzylthiocyclopentene-1-carboxamide and its sulfoxide (Formula II with $R=C_6H_{11}$ and $R_2=-CH_2C_6H_5$)

(a) 2-N-cyclohexyl benzylthio-1-cyclopentene-1-carboxamide

To a stirred solution, at ambient temperature and under an inert atmosphere, of 41 g of 2-N-cyclo-hexyl cyclopentanone carboxamide, and 37.3 g of paratoluene sulfonic acid (monohydrate) in 500 cm³ of glacial acetic acid, there are added 7.5 cm³ of benzylmercaptan. After two hours of stirring the mixture is left overnight at ambient temperature.

The reaction mixture is then concentrated under reduced pressure and dissolved in 600 cm³ of dichloromethane. The solution is washed with 2N soda until a basic pH of the wash waters is obtained and then with water until a neutral pH is achieved. The solution is then dried over magnesium sulfate, concentrated and then rapidly passed over a silica gel filter. After concentration of the filtrate 57 g of a solid are obtained which is then recrystallized in hexane in the presence of a trace amount of toluene, yielding 49 g of white crystals whose NMR spectrum corresponds to the expected structure.

Elemental analysis: $C_{19}H_{25}NOS$;
Calculated: C 72.33; H 7.99; N 4.44; O 5.08; S 10.16;
Found: C 72.40; H 8.03; N 4.28; O 5.08; S 10.21.

(b) 2-N-cyclohexyl benzylsulfinyl-1-cyclopentene-1-carboxamide

A suspension of 42 g of 2-N-cyclohexyl benzylsulfinyl-1-cyclopentene-1-carboxamide, obtained above, in 200 cm³ of formic acid is treated while stirring with 19 cm³ of 30% $H_2O_2$ at a temperature lower than 30° C. After two hours, the reaction mixture is left overnight at ambient temperature. After evaporation of the solvent under a vacuum, the product is dissolved in 250 cm³ of dichloromethane, washed with normal soda, then with water and finally dried over magnesium sulfate. After purification by silica gel chromatography, 25 g of 2-N-cyclohexyl benzylsulfinyl-1-cyclopentene-1- carboxamide in the form of white crystals having a melting point of 115° C. are obtained.

The NMR $^1$H spectrum corresponds to the expected structure.

EXAMPLE 13

Preparation of 2-N-p-chlorophenyl benzylthio-1-cyclopentene-1-carboxamide and its sulfoxide (Formula II with $R_1 = -C_6H_4pCl$ and $R_2 = -CH_2C_6H_5$)

(a) 2-N-p-chlorophenyl benzyl thio-1-cyclopentene-1-carboxamide.

To a suspension, with stirring, of 10 g of 2-benzylthio-1-cyclopentene-1-carboxylic acid, obtained in Example 2(a), in 200 cm$^3$ of methylene chloride there are slowly added at ambient temperature and under a nitrogen atmosphere, 7.7 cm$^3$ of thionyl chloride. The mixture is then held at the boiling temperature of the solvent until homogenization of the reaction mixture occurs. The reaction mixture is then evaporated to dryness to remove excess thionyl chloride.

The mixture is then taken up in 200 cm$^3$ of anhydrous methylene chloride and 10.86 g of p-chloroaniline are added. After 2 hours of stirring, the acid chloride is transformed into the corresponding amide. The solution is washed with 1N HCl, then three times with water and dried over magnesium sulfate. After evaporation of the solvent 16 g of crude amide are obtained which is then purified by passage through a silica gel column. The product is eluted with a 1:9 mixture of ethyl acetate/hexane, then recrystallized in ethyl acetate, yielding 9 g of 2-N-p-chlorophenyl benzylthio-1-cyclopentene-1-carboxamide in the form of white crystals having a melting point of 141° C.

Elemental analysis: $C_{19}H_{18}Cl\ NOS$;

Calculated: C 66.36; H 5.27; Cl 10.31; N 4.07; S 9.33;

Found: C 65.78; H 5.25; Cl 10.12; N 3.95; S 9.07.

(b) 2-N-p-chlorophenyl benzylsulfinyl-1-cyclopentene-1-carboxamide

To a suspension of 6.9 of the thioether, obtained above in 30 cm$^3$ of formic acid there are added 1.42 cm$^3$ of 30% $H_2O_2$ while maintaining the temperature lower than 30° C. The reaction is followed by silica gel chromatography (TLC).

The product is filtered and dried, yielding 5 g of 2-N-p chlorophenyl benzylsulfinyl-1-cyclopentene-1-carboxamide in the form of white crystals.

The NMR $^1$H spectrum corresponds to the expected structure.

EXAMPLE 14

Preparation of 2-N-p-chlorobenzyl benzylthio-1-cyclopentene-1-carboxamide and its sulfoxide (Formula II with $R_1 = -CH_2C_6H_4pCl$ and $R_2 = -CH_2C_6H_5$)

(a) 2-N-p-chlorobenzyl benzylthio-1-cyclopentene-1-carboxamide

In accordance with the same operating procedures as those described in Example 13(a), 10 g of 2-benzylthio-1-cyclopentene-1-carboxylic acid are transformed into the corresponding acid chloride and the latter is then treated with p-chlorobenzylamine.

12 g of 2-N-p-chlorobenzyl benzylthio-1-cyclopentyl-1-carboxamide are obtained in the form of white crystals having a melting point of 122° C.

(b) 2-N-p-chlorobenzyl benzylsulfinyl-1-cyclopentene-1-carboxamide 12 g of the thioether obtained above are treated with 2.70 cm$^3$ of 30% $H_2O_2$ in 60 cm$^3$ of formic acid.

At the end of the reaction, the formic acid is evaporated under reduced pressure. The resulting product is dissolved in 200 cm$^3$ of dichloromethane. The resulting solution is washed twice with 2N soda, then with water and dried over magnesium sulfate. After having evaporated the solvent, 11 g of 2-N-p-chlorobenzyl benzylsulfinyl-1-cyclopentene-1-carboxamide whose NMR $^1$H spectrum corresponds to the expected structure are obtained.

EXAMPLE 15

Preparation of 2',4'-N-dichloro-2-benzyl benzylthio-1-cyclopentene-1-carboxamides and its sulfoxide (Formula II with $R_1 = -CH_2C_6H_3Cl_2$ and $R_2 = -CH_2C_6H_5$)

(a) 2',4'-N-dichloro-2-benzyl benzylthio-1-cyclopentene-1-carboxamide.

To a suspension, with stirring, of 50 g of 2-benzylthio cyclopentene carboxylic acid, obtained in Example 2(a), in 500 cm$^3$ of anhydrous methylene chloride, there are slowly added, at 0° C. and under an inert atmosphere, 49.8 g of phosphorus pentachloride.

After the end of the addition the reaction mixture is held at reflux for 2½ hours. The solution is then evaporated to dryness to remove phosphorus oxychloride. The resulting crude acid chloride is dissolved in 250 cm$^3$ of anhydrous methylene chloride and this solution is then poured, with stirring at 0° C., into a mixture of 45 cm$^3$ of anhydrous triethylamine and 43 cm$^3$ of 2,4-dichlorobenzylamine in 300 cm$^3$ of methylene chloride.

After the end of the addition, the reaction mixture is again stirred for 3 hours at ambient temperature, washed with 1N HCl, then with sodium bicarbonate and finally with water. The solution of methylene chloride is dried over magnesium sulfate, treated with animal charcoal and concentrated.

The amide crystallizes by stirring in ether. The crystallized amide is filtered and dried, yielding 50 g of 2',4'-N-dichloro'2-benzyl benzylthio-1-cyclopentene-1-carboxamide in the form of a white solid having a melting point of 91° C.

Elemental analysis: $C_{20}H_{19}Cl_2NOS$;

Calculated: C 61.22; H 4.88; Cl 18.07; N 3.57; O 4.08; S 8.17;

Found: C 61.26; H 4.93; Cl 18.03; N 3.53; O 4.26; S 8.05.

(b) 2',4'-N-dichloro-2-benzyl benzylsulfinyl-1-cyclopentene-1-carboxamide

At a temperature lower than 10° C., 10.1 cm$^3$ of 30% $H_2O_2$ are added to a stirred suspension of 39 g of the thioether obtained above in 200 cm$^3$ of formic acid. After the end of the reaction, the reaction mixture is evaporated to dryness and the resulting solid is treated in suspension in water with sodium bicarbonate. The solid is then filtered, washed with water and dried, yielding 39 g of 2',4'-dichloro-2-benzyl benzylsulfinyl-1-cyclopentene-1-carboxamide in the form of a white powder having a melting point of 170° C.

Elemental analysis: $C_{20}H_{19}Cl_2NO_2S$;

Calculated: C 58.82; H 4.69; Cl 17.36; N 3.43; O 7.83; S 7.85;

Found: C 58.79; H 4.70; Cl 17.50; N 3.35; O 7.66; S 7.90.

II. Preparation of 4,5-tri- and tetra-methylene-4-isothiazoline-3-ones.

EXAMPLE 1'

Preparation of 4,5-trimethylene-4-isothiazoline-3-one (a) 4,5-trimethylene-4-isothiazoline-3-one hydrochloride.

To a solution, with stirring, of 210 g of 2-benzyl-sulfinyl-1-cyclopentene-1-carboxamide, obtained in Example 1(b), in 1 liter of pure dichloromethane there are slowly added at a temperature lower than 10° C., 65 cm$^3$ of thionyl chloride over a period of about 1 hour.

About one hour after the end of the addition, it is verified by TLC that all of the starting sulfoxide has been transformed. The product remaining in solution is precipitated at 0° C. by the addition of one liter of ether to the reaction mixture. The precipitated solid is filtered, washed with acetonitrile and then dried, yielding 126 g of 4,5-trimethylene-4-isothiazoline-3-one-hydrochloride in the form of beige crystals having a melting point of 168° C.

The IR and NMR $^1$H spectra correspond to the expected structure.

(b) 4,5-trimethylene-4-isothiazoline-3-one.

The pH of a suspension, stirred at ambient temperature, of 120 g of the preceding hydrochloride in 500 cm$^3$ of water is adjusted to about 6 by the addition of sodium bicarbonate. The product is then filtered, washed several times with water and then dried. After verification of the absence of chloride ions, 90 g of 4,5-trimethylene-4-isothiazoline-3-one are obtained in the form of gray crystals that are recrystallized in an acetic acid/ethylacetate mixture. After recrystallization 55 g of slightly beige crystals having a melting point of 190° C. are obtained.

The NMR $^1$H spectrum corresponds to the expected structure.

Elemental analysis: $C_6H_7NOS$;
Calculated: C 51.04; H 5.00; N 9.92; O 11.93; S 22.71;
Found: C 50.86; H 4.88; N 10.04; O 12.02; S 22.48.

EXAMPLE 2'

Preparation of 2-methyl-4,5-trimethylene-4-isothiazoline-3-one (hydrochloride)

A solution of 143 g of the sulfoxide obtained in Example 2(c) in 400 cm$^3$ of anhydrous methylene chloride is stirred at 0° C. under an inert atmosphere.

To this colorless solution there are slowly added 47 cm$^3$ of thionyl chloride. The product beings to precipitate when two thirds of the thionyl chloride has been added. One half hour after the end of the addition it is verified by TLC that all of the sulfoxide is transformed into the corresponding 4-isothiazoline-3-one.

To the reaction mixture 150 cm$^3$ of isopropyl ether are then added. The resulting solid is filtered and then dried. The dried solid is then stirred in 250 cm$^3$ of acetone for one-half hour.

After filtering and drying the solid, 91 g of white crystals of the expected hydrochloride having a melting point of 156° C. (decomposition) are obtained.

The NMR $^1$H spectrum corresponds to the expected structure.

Elemental analysis: $C_7H_{10}Cl\ NOS$;
Calculated: C 43.86; H 5.26; N 7.31; Cl 18.49; O 8.35; S 16.73;
Found: C 43.58; H 5.26; N 7.31; Cl 18.65; O 8.44; S 16.52.

EXAMPLE 3'

Preparation of 2-ethyl-4,5-trimethylene-4-isothiazoline-3-one (hydrochloride)

In accordance with the same procedures as described in Example 2', 60 g of 2-N-ethyl benzylsulfinyl-1-cyclopentene-1-carboxamide, obtained in Example 3(b), are treated with 19.3 cm$^3$ of thionyl chloride. After precipitation by the addition of isopropyl ether, 27 g of 2-ethyl-4,5-trimethylene-4-isothiazoline-3-one hydrochloride in the form of white crystals having a melting point of 122° C. are obtained. This product is provided in hemihydrate form.

The NMR $^1$H spectrum corresponds to the expected structure.

Elemental analysis: $C_8H_{12}Cl\ NOS/0.5\ H_2O$;
Calculated: C 44.75; H 6.10; N 6.52; S 14.94;
Found: C 44.62; H 6.22; N 6.61; S 14.56.

EXAMPLE 4'

Preparation of 2-n-butyl-4,5-trimethylene-4-isothiazoline-3-one (hydrochloride)

To a solution, while stirring at 0° C., of 305.4 g of 2-N-butyl benzylsulfinyl-1-cyclopentene-1-carboxamide, obtained in Example 4(b), in one liter of methylene chloride, there are slowly added 86 cm$^3$ of thionyl chloride over a period of about 1 hour. About one-half hour after the end of the addition it is verified by TLC that all of the sulfoxide is transformed. There are then introduced, at 15° C., and with stirring, 500 cm$^3$ of isopropyl ether. The hydrochloride crystallizes and there are introduced after about one hour 500 cm$^3$ of isopropyl ether. The reaction mixture is then cooled to 5° C. The resulting crystals are filtered, washed with isopropyl ether and then dried, yielding 210 g of 2-n-butyl-4,5-trimethylene-4-isothiazoline-3-one hydrochloride in the form of a beige solid having a melting point of 109° C.

The NMR $^1$H spectrum corresponds to the expected structure.

Elemental analysis: $C_{10}H_{16}Cl\ NOS$;
Calculated: C 51.38; H 6.90; Cl 15.17; N 5.99; O 6.84; S 13.71;
Found: C 51.37; H 6.89; Cl 15.07; N 6.00; O 6.92; S 13.66.

EXAMPLE 5'

Preparation of 2-tert.butyl-4,5-trimethylene-4-isothiazoline-3-one (a) 2-tert.butyl-4,5-trimethylene-4-isothiazoline-3-one To a solution of 63.5 g of 2-N-tert.butyl benzylsulfinyl-1-cyclopentene-1-carboxamide, obtained in Example 5(b), in 120 cm$^3$ of methylene chloride there are slowly added, while stirring at 0° C. 18.2 cm$^3$ of thionyl chloride. One-half hour after the end of the addition, it is verified by TLC that all of the initial reactant is transformed. There are then added at 0° C., with sitrring, 380 cm$^3$ of ethyl ether. The crystallized product is filtered, washed twice with ether and dried, yielding 44 g of 2-tert.butyl-4,5-trimethylene-4-isothiazoline-3-one hydrochloride in the form of white crystals having a melting point of about 90° C. (decomposition).

Elemental analysis: $C_{10}H_{16}Cl\ NOS$;
Calculated: C 51.38; H 6.90; Cl 15.17; N 5.99; S 13.71;

Found: C 50.98; H 6.88; Cl 14.99; N 5.91; S 13.47.

(b) 2-tert.butyl-4,5-trimethylene-4-isothiazoline-3-one

A solution of 39 g of the preceding hydrochloride in 600 cm$^3$ of methylene chloride is stirred at ambient temperature. 150 cm$^3$ of water are then added and the stirring is continued for ¼ hour. The organic phase is decanted, then treated twice under the same conditions with 150 cm$^3$ of water, dried over magnesium sulfate and filtered. The solvent is removed by evaporation under a vacuum. After cooling, 32 g of 2-tert.butyl-4,5-trimethylene-4-isothiazoline-3-one in the form of a white powder having a melting point of 99° C. are obtained.

Elemental analysis: $C_{10}H_{15}NOS$;
Calculated: C 60.87; H 7.66; N 7.10; S 16.25;
Found: C 60.49; H 7.73; N 7.06; S 16.13.

EXAMPLE 6'

Preparation of 2-isopropyl-4,5-trimethylene-4-isothiazoline-3-one (hydrochloride)

In accordance with the same procedures described in Example 2', 157 g of 2-N-isopropyl benzylsulfinyl-1-cyclopentene-1-carboxamide, obtained in Example 6(b), in 400 cm$^3$ of dimethylene chloride, are treated with 47 cm$^3$ of thionyl chloride.

The product is precipitated with isopropyl ether and hexane, and then recrystallized in a 4:1 mixture of hexane/ethyl acetate, yielding 84 g of 2-isopropyl-4,5-trimethylene-4-isothiazoline-3-one hydrochloride having a melting point of 112° C.

The NMR $^1$H spectrum corresponds to the expected structure.

Elemental analysis: $C_9H_{14}Cl\ NOS$;
Calculated: C 49.20; H 6.42; Cl 16.14; N 6.35; O 7.28; S 14.59;
Found: C 49.26; H 6.34; Cl 16.09; N 6.41; O 7.39; S 14.48.

EXAMPLE 7'

Preparation of 2-n-hexyl-4,5-trimethylene-4-isothiazoline-3-one (a) 2-n-hexyl-4,5-trimethylene-4-isothiazoline-3-one hydrochloride To a solution of 158 g of 2-N-hexyl benzylsulfinyl-1-cyclopentene-1-carboxamide, obtained in Example 7(b), in 500 cm$^3$ of dichloromethane cooled to 0° C., there are slowly added 45 cm$^3$ of thionyl chloride. When all of the initial reactant is transformed, 1.5 liters of ethyl ether are added with stirring. The expected hydrochloride crystallizes and after filtering and washing the same with ether, 85 g of 2-n-hexyl 4,5-trimethylene-4-isothiazoline-3-one hydrochloride in the form of beige crystals are obtained.

Elemental analysis: $C_{12}H_{20}Cl\ NOS$;
Calculated: C 55.05; H 7.70; Cl 13.54; N 5.35; S 12.25;
Found: C 55.20; H 7.76; Cl 13.48; N 5.41; S 12.10.

(b) 2-n-hexyl-4,5-trimethylene-4-isothiazoline-3-one

To a stirred solution at 0° C. of 83 g of the preceding hydrochloride in 800 cm$^3$ of dichloromethane, 200 cm$^3$ of water are added. After ¼ hour of stirring, the organic phase is decanted, then treated twice under the same conditions with the same volume of water. The dichloromethane phase is dried over magnesium sulfate and the solvent is removed by evaporation under reduced pressure. The resulting product in the form of a viscous liquid is crystallized in hexane cooled to −20° C., yielding 50 g of 2-n-hexyl-4,5-trimethylene-4-isothiazoline-3-one in the form of beige crystals having a melting point of 28° C.

Elemental analysis corresponds to a partially hydrated product: $C_{12}H_{19}NOS\cdot\frac{1}{4}H_2O$;
Calculated: C 62.70; H 8.55; N 6.09; S 13.95;
Found: C 63.01; H 8.84; N 6.01; S 13.69.

EXAMPLE 8'

Preparation of 2-octyl-4,5-trimethylene-4-isothiazoline-3-one (a) 2-octyl-4,5-trimethylene-4-isothiazoline-3-one hydrochloride In accordance with the same procedures described in Example 2', 1 kg of 2-N-octyl benzylsulfinyl-1-cyclopentene-1-carboxamide, obtained in Example 8(b), in 3 liters of methylene chloride are treated with 220 cm$^3$ of thionyl chloride.

After precipitation by the addition of isopropyl ether, 650 g of 2-octyl-4,5-trimethylene-4-isothiazoline-3-one hydrochloride in the form of fine white crystals having a melting point of 96° C. are obtained.

Elemental analysis: $C_{14}H_{24}Cl\ NOS$;
Calculated: C 58.01; H 8.35; Cl 12.23; N 4.83; O 5.52; S 11.06;
Found: C 58.30; H 8.31; Cl 12.30; N 4.91; O 5.58; S 10.88.

(b) 2-octyl-4,5-trimethylene-4-isothiazoline-3-one

To a solution of 1 kg of 2-octyl-4,5-trimethylene-4-isothiazoline-3-one hydrochloride, obtained above, in 2.5 liters of methylene chloride there is added, at ambient temperature and away from light, 1 liter of water. Stirring is continued for 15 minutes and the aqueous phase is decanted. The organic phase is treated three times with water under the same conditions. At the last washing the pH is neutral and the test for chlorides is negative (silver nitrate test).

The organic phase is then dried over magnesium sulfate and the methylene chloride evaporated under reduced pressure, yielding a brown colored viscous liquid that is then dissolved in 500 cm$^3$ of hexane at ambient temperature.

On cooling the resulting solution to −20° C. the product crystallizes. The crystals are filtered and dried under reduced pressure at ambient temperature yeilding 700 g of 2-octyl-4,5-trimethylene-4-isothiazoline-3-one in the form of light beige crystals having a melting point of 36° C.

Elemental analysis: $C_{14}H_{23}NOS$;
Calculated: C 66.35; H 9.15; N 5.53; O 6.31; S 12.65;
Found: C 65.88; H 9.46; N 5.50; O 6.86; S 12.49.

Example 9'

Preparation of 2-n-decyl-4,5-trimethylene-4-isothiazoline-3-one (a) 2-n-decyl-4,5-trimethylene-4-isothiazoline-3-one hydrochloride To a stirred solution at 0° C. of 50 g of 2-N-decyl benzylsulfinyl-1-cyclopentene-1-carboxamide, obtained in Example 9(b), in 100 cm$^3$ of methylene chloride there are slowly added 12 cm$^3$ of thionyl chloride. One quarter hour later, all of the initial reactant is transformed. There are then added, with stirring, 200 cm$^3$ of isopropyl ether. The hydrochloride crystallizes, and the crystals are filtered, washed twice with ether and dried, yielding 37 g of 2-n-decyl-4,5-trimethylene-4-isothiazoline-3-one hydrochloride in the form of white crystals having a melting point of 102° C.

Elemental analysis: $C_{16}H_{28}Cl\ NOS$;
Calculated: C 60.44; H 8.87; Cl 11.15; N 4.41; S 10.09;
Found: C 60.49; H 8.85; Cl 11.10; N 4.32; S 9.94.

(b) 2-n-decyl-4,5-trimethylene-4-isothiazoline-3-one

A solution of 35 g of the preceding hydrochloride in 100 cm$^3$ of methylene chloride is stirred with 100 cm$^3$ of water for ¼ hour.

The organic phase is decanted, then treated again twice with the same volume of water. The resulting solution is dried over magnesium sulfate and the solvent is removed by evaporation under a vacuum. The resulting solution is then cooled to −20° C. The crystallized 2-n-decyl-4,5-trimethylene-4-isothiazoline-3-one is filtered and dried, yielding 26 g of beige crystals having a melting point of 48° C.

Elemental analysis: $C_{16}H_{27}\ NOS$;
Calculated: C 68.27; H 9.67; N 4.98; S 11.39;
Found: C 68.18; H 9.64; N 4.93; S 11.18.

EXAMPLE 10'

Preparation of
2-n-dodecyl-4,5-trimethylene-4-isothiazoline-3-one (a) 2-n-dodecyl-4,5-trimethylene-4-isothiazoline-3-one hydrochloride In accordance with the same procedures described in Example 2', 90 g of 2-N-dodecyl benzylsulfinyl-1-cyclopentene-1-carboxamide, obtained in Example 10(b), are treated with 18.8 cm$^3$ of thionyl chloride.

On precipitation with isopropyl ether, 68 g of 2-n-dodecyl-4,5-trimethylene-4-isothiazoline-3-one hydrochloride in the form of white crystals having a melting point of 102° C. are obtained.

Elemental analysis: $C_{18}H_{32}Cl\ NOS$;
Calculated: C 62.48; H 9.32; Cl 10.25; N 4.06; O 4.62; S 9.27;
Found: C 62.42; H 9.33; Cl 10.26; N 4.02; O 4.72; S 9.14.

(b) 2-n-dodecyl-4,5-trimethylene-4-isothiazoline-3-one

In accordance with the same procedures described in Example 6'(b), 68 g of the preceding hydrochloride, in 300 cm$^3$ of methylene chloride are stirred in the presence of 120 cm$^3$ of water for 1 hour.

After treatment under the same conditions and recrystallization in isopropyl ether, 40 g of 2-n-dodecyl-4,5-trimethylene-4-isothiazoline-3-one in the form of white crystals having a melting point of 54° C. are obtained.

Elemental analysis: $C_{18}H_{31}\ NOS$;
Calculated: C 69.85; H 10.09; N 4.52; O 5.17; S 10.36;
Found: C 69.88; H 10.16; N 4.45; O 5.11; S 10.28.

EXAMPLE 11'

Preparation of
2-allyl-4,5-trimethylene-4-isothiazoline-3-one (a) 2-allyl-4,5-trimethylene-4-isothiazoline-3-one hydrochloride To a solution of 40 g of 2-N-allyl benzylsulfinyl-1-cyclopentene-1-carboxamide, obtained in Example 11(b), in 80 cm$^3$ of methylene chloride cooled to 0° C. there are slowly added 12 cm$^3$ of thionyl chloride. One quarter hour later it is verified by TLC that the sulfoxide is completely transformed. There is then slowly added isopropyl ether until the appearance of a cloud persists in the reaction mixture. At this stage stirring is maintained for 2 hours to disperse the crystals. These latter are filtered and dissovled in 50 cm$^3$ of methylne chloride.

To this vigorously stirred solution there are slowly added 30 cm$^3$ of isopropyl ether. The crystallized product is rapidly filtered (hygroscopic product), washed with isorpopyl ether and dried.

25 g of cream colored crystals having a melting point of 86° C. (decomposition) are obtained.

Elemental analysis corresponds to a hemi-hydrate: $C_9H_{12}Cl\ NOS\cdot\tfrac{1}{2}H_2O$;
Calculated: C 47.67; H 5.78; Cl 15.64; N 6.18; S 14.14;
Found: C 47.80; H 5.62; Cl 15.88; N 6.15; S 14.25.

(b) 2-allyl-4,5-trimethylene-4-isothiazoline-3-one

To a stirred solution, at ambient temperature, of 22 g of the preceding hydrochloride in 80 cm$^3$ of methylene chloride there are added 30 cm$^3$ of water. Stirring is continued for one quarter hour. The organic phase is decanted, then treated again twice under the same conditions with 30 cm$^3$ of water. The methylene chloride phase is dried over magnesium sulfate, then evaporated under reduced pressure. The resulting liquid is treated with animal charcoal, in solution in boiling isopropyl ether. The solution is filtered then cooled to 0° C. The crystals are filtered and dried, yielding 20 g of 2-allyl-4,5-trimethylene-4-isothiazoline-3-one in the form of a cream colored solid having a melting point of 55° C.

Elemental analysis: $C_9H_{11}NOS$;
Calculated: C 59.63; H 6.12; N 7.73; S 17.69;
Found: C 59.65; H 6.14; N 7.77; S 17.48.

EXAMPLE 12'

Preparation of
2-cyclohexyl-4,5-trimethylene-4-isothiazoline-3-one

A solution of 5 g of 2-N-cyclohexyl benzylsulfinyl-1-cyclopentene-1-carboxamide, obtained in Example 12(b), in 25 cm$^3$ of dichloromethane is treated, with stirring at 0° C. and under an inert atmosphere, with 1.30 cm$^3$ of thionyl chloride. When all of the sulfoxide is transformed, 2.5 cm$^3$ of triethylamine are added. The reaction mixture is then diluted with 15 cm$^3$ of dichloromethane. After washing with water, the organic phase is decanted, dried over magnesium sulfate and introduced into a silica gel column. The expected product is eluted with a 1:1 mixture of methylene chloride/ethyl acetate. After concentration of the elution phases, 1.50 g of 2-cyclohexyl-4,5-trimethylene-4-isothiazoline-3-one in the form of beige crystals having a melting point of 70° C. are recovered.

The IR and NMR $^1$H spectra correspond to the structure.

Elemental analysis: $C_{12}H_{17}\ NOS$;
Calcualted: C 64.53; H 7.67; N 6.27; O 7.16; S 14.36;
Found: C 64.63; H 7.72; N 6.19; O 7.15; S 14.11.

EXAMPLE 13'

Preparation of
2-p-chlorophenyl-4,5-trimethylene-4-isothiazoline-3-one

To a suspension of 5 g of the sulfoxide obtained in Example 13(b) in 30 cm$^3$ of anhydrous methylene chloride, there are slowly added 1.2 cm$^3$ of thionyl chloride. The reaction mixture becomes homogeneous and the hydrochloride rapidly precipitates. 50 cm$^3$ of ether are then added to complete the crystallization. The resulting precipitate is filtered, washed with ether and suspended in 100 cm$^3$ of water. The pH of this suspension is adjusted to 7-8 by the addition of sodium bicarbonate.

The solid is filtered again, washed with water, then oven dried at 100° C. After dissolving the resulting solid in 150 cm³ of methylene chloride and treating with 2 g of silica gel, the silica is filtered and the filtrate is evaporated to dryness, yielding 2.5 g of 2-p-chlorophenyl-4,5-trimethylene-4-isothiazoline-3-one in the form of cream colored crystals having a melting point of 177° C. The IR and NMR ¹H spectra correspond to the expected structure.

Elemental analysis: $C_{12}H_{10}Cl\ NOS$;
Calculated: C 57.25; H 4.00; Cl 14.08; N 5.56; O 6.35; S 12.74;
Found: C 57.41; H 3.97; Cl 14.00; N 5.50; O 6.50; S 12.82.

EXAMPLE 14'

Preparation of 2-p-chlorobenzyl-4,5-trimethylene-4-isothiazoline-3-one (a) 2-p-chlorobenzyl-4,5-trimethylene-4-isothiazoline-3-one hydrochloride To a solution of 5.4 g of the sulfoxide obtained in Example 14(b) in 15 cm³ of stirred methylene chloride, there are added under an inert atmosphere 1.23 cm³ of thionyl chloride. The mixture is then left one hour at 20° C. On addition of 200 cm³ ether, the hydrochloride precipitates, and it is then filtered and dried, yielding 3.6 g of 2-p-chlorobenzyl-4,5-trimethylene-4-isothiazoline-3-one hydrochloride in the form of a white solid whose NMR ¹H spectrum corresponds to the expected structure.

(b) 2-p-chlorobenzyl-4,5-trimethylene-4-isothiazoline-3-one.

To a suspension of 3.3 g of the preceding hydrochloride in 50 cm³ of water there is slowly added an aqueous solution of sodium bicarbonate so as to adjust the pH between 8 and 9. The solid is filtered, washed with water and dried, yielding 2.8 g of 2-p-chlorobenzyl-4,5-trimethylene-4-isothiazoline-3-one in the form of a light beige solid having a melting point of 105° C.

The IR and NMR ¹H spectra correspond to the expected structure.

Elemental analysis: $C_{13}H_{12}Cl\ NOS$;
Calculated: C 58.75; H 4.55; Cl 13.34; N 5.27; O 6.02; S 12.06;
Found: C 58.55; H 4.52; Cl 13.29; N 5.21; O 6.20; S 12.15.

EXAMPLE 15'

Preparation of 2',4'-dichloro-2-benzyl-4,5-trimethylene-4-isothiazoline-3-one (a) 2',4'-dichloro-2-benzyl-4,5-trimethylene-4-isothiazoline-3-one hydrochloride 35 g of the sulfoxide obtained in Example 15(b) in 200 cm³ of anhydrous methylene chloride are treated with 7.5 cm³ of thionyl chloride under same conditions as described in Example 10'(a), yielding 23 g of 2',4'-dichloro-2-benzyl-4,5-trimethylene-4-isothiazoline-3-one hydrochloride in the form of white crystals (decomposition temperature −164° C.).

The NMR ¹H spectrum corresponds to the expected structure.

(b) 2',4'-dichloro-2-benzyl-4,5-trimethylene-4-isothiazoline-3-one

Starting with 16 g of the preceding hydrochloride treated under the same conditions as those of Example 10'(b) 13 g of 2',4'-dichloro-2-benzyl-4,5-trimethylene-4-isothiazoline-3-one in the form of white crystals having a melting point of 131° C. are obtained.

Elemental analysis: $C_{13}H_{11}Cl_2\ NOS$;
Calculated: C 52.00; H 3.69; Cl 23.62; N 4.66; O 5.33; S 10.68;
Found: C 52.07; H 3.74; Cl 23.33; N 4.67; O 5.26; S 10.74.

What is claimed is:

1. A process for preparing a 4,5-tri or tetramethylene-4-isothiazoline-3-one having the formula

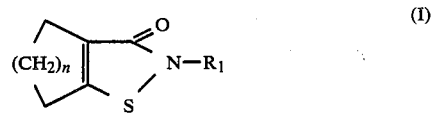

wherein
$R_1$ represents (i) hydrogen, (ii) linear or branched alkyl having 1–12 carbon atoms, (iii) alkenyl having 3–6 carbon atoms, (iv) cycloalkyl having 3–6 carbon atoms or (v)

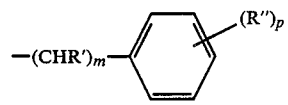

wherein m is 0 or 1, p is 1 or 2, R' represents hydrogen or lower alkyl and R" represents hydrogen, lower alkyl, $NO_2$, $-CF_3$ or halogen, and n is 1 or 2, said process comprising the steps of
(a) reacting a compound of the formula

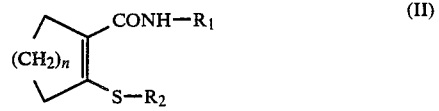

wherein
$R_1$ and n have the same meaning given above, and
$R_2$ is benzyl with m-chloroperbenzoic acid or hydrogen peroxide in an acid medium so as to produce the sulfoxide of said compound, and
(b) cyclizing said sulfoxide in an organic solvent in the presence of an acid chloride so as to produce a 4,5-tri or tetramethylene-4-isothiazoline-3-one hydrochloride and adding to said hydrochloride a mineral or organic base or water so as to free the 4,5-tri or tetramethylene-4-isothiazoline-3-one in the form of a free base.

2. The process of claim 1 wherein the acid medium is (a) formic acid for the most polar amides of formula II or (b) a mixture of methylene chloride containing formic acid for the less polar amides of formula II.

3. The process of claim 1 wherein said sulfoxide of the compound of formula II is cyclized in methylene chloride in the presence of thionylchloride.

* * * * *